US012806023B2

(12) United States Patent
Chiang et al.

(10) Patent No.: US 12,806,023 B2
(45) Date of Patent: Nov. 24, 2026

(54) INTERVERTEBRAL DISC ANNULUS FIBROSUS IMPLANT AND METHOD FOR PREPARING THE SAME

(71) Applicant: TAIPEI MEDICAL UNIVERSITY, Taipei City (TW)

(72) Inventors: Chang-Jung Chiang, Taipei City (TW); Yang-Hwei Tsuang, Taipei City (TW); Lien-Chen Wu, Taipei City (TW); Yueh-Ying Hsieh, Taipei City (TW); Po-Yi Liu, Taipei City (TW)

(73) Assignee: TAIPEI MEDICAL UNIVERSITY, Taipei City (TW)

( * ) Notice: Subject to any disclaimer, the term of this patent is extended or adjusted under 35 U.S.C. 154(b) by 36 days.

(21) Appl. No.: 18/907,336

(22) Filed: Oct. 4, 2024

(65) Prior Publication Data

US 2025/0114204 A1 Apr. 10, 2025

Related U.S. Application Data

(60) Provisional application No. 63/588,431, filed on Oct. 6, 2023.

(51) Int. Cl.
*A61F 2/30* (2006.01)
*A61F 2/44* (2006.01)

(52) U.S. Cl.
CPC .... *A61F 2/3094* (2013.01); *A61F 2002/4435* (2013.01)

(58) Field of Classification Search
CPC .................... A61F 2/442; A61F 2/3094; A61F 2002/4435; A61F 2002/444; A61F 2002/4445; A61F 2002/445
See application file for complete search history.

(56) References Cited

U.S. PATENT DOCUMENTS

2003/0114930 A1* 6/2003 Lim ........................ A61F 2/442 623/17.11
2004/0039392 A1* 2/2004 Trieu ...................... A61F 2/442 606/86 R (Continued)

FOREIGN PATENT DOCUMENTS

WO WO-2010000482 A1 * 1/2010 ............. A61F 2/442
WO WO-2013116624 A1 * 8/2013 ............. B32B 27/02
WO WO-2022076422 A1 * 4/2022 ......... A61F 2/30723

*Primary Examiner* — Eduardo C Robert
*Assistant Examiner* — Anna V. Little
(74) *Attorney, Agent, or Firm* — Studebaker Brackett PLLC

(57) ABSTRACT

Provided is a method for preparing an intervertebral disc annulus fibrosus implant, including: obtaining a sample having a plurality of ring-shaped collagen fiber layers; cutting and shaping the sample into a column having a top surface, an opposite bottom surface, and a peripheral surface connecting the top surface and the opposite bottom surface, wherein an area of the top surface is smaller than the area of the bottom surface; removing cells in the column; disinfecting, drying and shaping the column to prepare an column-shaped intervertebral disc annulus fibrosus implant. The present disclosure further provides an intervertebral disc annulus fibrosus implant and a method for transplanting an intervertebral disc annulus fibrosus implant. The disclosure can repair the damage of the intervertebral disc fibrous annulus and prevent the leakage of gel-like materials in the nucleus pulposus.

6 Claims, 7 Drawing Sheets

(56) References Cited

U.S. PATENT DOCUMENTS

| | | | | |
|---|---|---|---|---|
| 2007/0299520 A1* | 12/2007 | Trieu | A61F 2/30767 | 623/901 |
| 2008/0065218 A1* | 3/2008 | O'Neil | A61F 2/442 | 623/17.16 |
| 2008/0114458 A1* | 5/2008 | McKay | A61F 2/4611 | 606/108 |
| 2009/0234457 A1* | 9/2009 | Lotz | A61L 27/52 | 623/1.15 |
| 2011/0004311 A1* | 1/2011 | Semler | A61F 2/3872 | 623/17.16 |
| 2011/0098826 A1* | 4/2011 | Mauck | A61F 2/3094 | 623/23.72 |
| 2018/0228938 A1* | 8/2018 | McGuire | A61L 27/3662 | |
| 2020/0113705 A1* | 4/2020 | Francis | A61B 17/8855 | |

* cited by examiner

INTERVERTEBRAL DISC ANNULUS FIBROSUS IMPLANT AND METHOD FOR PREPARING THE SAME

BACKGROUND

1. Technical Field

The present disclosure relates to a technical field of intervertebral disc annulus fibrosus implants, which is contributed in the treatments of intervertebral disc annulus fibrosus damage and intervertebral disc herniation.

2. Description of Associated Art

An intervertebral disc is a fibrocartilage disc connecting two adjacent vertebrae to allow the vertebrae to move at certain angles appropriately, and functions as a shock absorber to provide a buffering effect between the two vertebrae. An intervertebral disc comprises two portions. The peripheral portion is annulus fibrosis, which is a dense tissue formed by a plurality of layers of ring-shaped and radial collagenous fibers and elastic fibers interwoven and arranged in concentric circles, and connects two adjacent vertebrae tightly. The central portion is a nucleus pulposus, which is a flexible, tensile gelatinous substance filling the space surrounded by the upper and lower cartilage plates and the annulus fibrosus, and being a residue of embryonic notochord, can provide a buffering effect against the force and impact to the vertebral column.

Intervetebral disc may be denatured or damaged due to aging, trauma, diseases, etc. The annulus fibrosus cannot protect the inner nucleus pulposus sufficiently when the annulus fibrosus is damaged, e.g., peripheral stripping and radical breaks, resulting in the leakage or protrusion of the nucleus pulposus. This may further constrict adjacent medulla spinalis or nerve root and cause back pain as well as pain and numbness in hands and feet, thereby resulting in vertebral diseases such as an intervertebral disc herniation (also called herniation of intervertebral disc, HIVD).

One of the treatments for intervertebral disc herniation is microendoscopic discectomy. However, there is a high risk of recurrence after microendoscopic discectomy. At re-operation, it is difficult to confirm the positions of spinal nerves since they may be embedded in the scar tissue formed after the first operation. Artificial intervertebral disc implants have been developed, including those made of ceramics, alloys, polymers, or a combination thereof. Also, artificial intervertebral disc implants formed by tissue engineering have been developed. However, there is still no intervertebral disc annulus fibrosus implant comparable to the innate intervertebral disc annulus fibrosus, providing similar composition, structure, and mechanical properties and promoting rapid wound healing of the annulus fibrosus.

SUMMARY

Given this, the first aspect of the present disclosure provides a method for preparing an intervertebral disc annulus fibrosus implant, comprising: obtaining a sample having a plurality of ring-shaped collagen fiber layers; cutting the sample into a column, wherein the column has a top surface, an opposite bottom surface, and a peripheral surface connecting the top surface and the bottom surface, and an area of the top surface is smaller than that of the bottom surface; removing cells from the column; disinfecting the column from which the cells have been removed, and drying the disinfected column to prepare the intervertebral disc annulus fibrosus implant.

In an embodiment, the top surface and the bottom surface are each independently circular or polygonal.

In an embodiment, the plurality of ring-shaped collagen fiber layers have an interlayer density increased along a direction from the top surface to the bottom surface.

In an embodiment, the plurality of ring-shaped collagen fiber layers have a type I collagen content increased along a direction from the top surface to the bottom surface.

In an embodiment, the sample is derived from an intervertebral disc of a vertebrate or an artificially cultured intervertebral disc annulus fibrosus mimic. In another embodiment, the vertebrate is a human, a pig, an orangutan, an ape or a monkey.

In an embodiment, the step of removing cells comprises soaking the column in a cell-removal solution containing a surfactant, a chelating agent and saline. In a further embodiment, the surfactant is at least one selected from the group consisting of 3-cholaminopropyldimethylamino-1-propyl sulfonate (CHAPS), NP-40, Tween-20, Triton X-100 and sodium dodecyl sulfonate (SDS); and the chelating agent is at least one selected from the group consisting of ethylenediaminetetraacetic acid (EDTA), ethylene glycol tetraacetic acid (EGTA) and ethylene diamine.

In an embodiment, the step of disinfecting comprises soaking the column in an antibiotic solution. In a further embodiment, the antibiotic solution comprises amphotericin B, gentamicine and vancomycin. In a further embodiment, the antibiotic solution comprises 2.5 μg/mL of amphotericin B, 50 μg/mL of gentamicine and 500 μg/mL of vancomycin.

In a further embodiment, the steps of removing cells and/or disinfecting are performed on a shaker at a rate of 50-200 rpm.

In an embodiment, the step of drying is performed by freeze-drying.

In an embodiment, the method further comprises after disinfecting the column, washing the disinfected column with saline to remove the cell-removal solution and the antibiotic solution.

The second aspect of the present disclosure further provides an intervertebral disc annulus fibrosus implant, which is a column having a plurality of ring-shaped collagen fiber layers, wherein the column has a top surface, a bottom surface, and a peripheral surface connecting the top surface and the bottom surface, wherein an area of the top surface is smaller than that of the bottom surface, and the intervertebral disc annulus fibrosus implant is substantially free of cells, water and microorganisms.

In an embodiment, the top surface and the bottom surface are each independently circular or polygonal.

In an embodiment, the plurality of ring-shaped collagen fiber layers have an interlayer density increased along a direction from the top surface to the bottom surface.

In an embodiment, the plurality of ring-shaped collagen fiber layers have a type I collagen content increased along a direction from the top surface to the bottom surface.

In an embodiment, the intervertebral disc annulus fibrosus implant is derived from an intervertebral disc of a vertebrate or an artificially cultured intervertebral disc annulus fibrosus mimic. In another embodiment, the vertebrate is a human, a pig, an orangutan, an ape or a monkey.

In an embodiment, the column has a length of 6-8 mm, and a maximum width of 3-5 mm.

In an embodiment, the intervertebral disc annulus fibrosus implant expands after contacting water to fill a wound caused by damage.

The third aspect of the present disclosure further provides a method for transplanting an intervertebral disc annulus fibrosus implant, comprising:

- obtaining an intervertebral disc annulus fibrosus implant of the present disclosure, wherein the intervertebral disc annulus fibrosus implant has a column formed with a plurality of ring-shaped collagen fiber layers and has a top surface, an opposite bottom surface, and a peripheral surface connecting the top surface and the bottom surface, wherein an area of the top surface is smaller than that of the bottom surface;
- preparing a transplanting device, which comprises a holding part, a long needle located on the top of the holding part, and a movable base between the holding part and the long needle;
- inserting the long needle into the intervertebral disc annulus fibrosus implant from the top surface until the top surface contacts the movable base;
- moving the transplanting device to move the intervertebral disc annulus fibrosus implant to a target position; and
- moving the movable base along the long needle to locate the intervertebral disc annulus fibrosus implant to the target position and leaving it at the target position.

In an embodiment, after the intervertebral disc annulus fibrosus implant is left at the target position, the intervertebral disc annulus fibrosus implant contacts water in the tissue fluid at the target position and expands to fill the target position.

In an embodiment, the top surface and the bottom surface are each independently circular or polygonal.

In an embodiment, the plurality of ring-shaped collagen fiber layers have an interlayer density increased along a direction from the top surface to the bottom surface.

In an embodiment, the plurality of ring-shaped collagen fiber layers have a type I collagen content increased along a direction from the top surface to the bottom surface.

Therefore, the intervertebral disc annulus fibrosus implant of the present disclosure can provide treatments effective in the clinic, which can be used for impairing the damage in intervertebral disc annulus fibrosus to prevent the gelatinous substance in the nucleus pulposus from leaking or protruding. In addition, the method for transplanting the intervertebral disc annulus fibrosus implant of the present disclosure can effectively fix the implant by placing the intervertebral disc annulus fibrosus implant at the transplanting site in a particular manner and promote wound healing.

DETAILED DESCRIPTION OF THE PREFERRED EMBODIMENTS

The execution modes of the present disclosure will be illustrated by following specific embodiments, one having ordinary skill in the art can easily realize the advantages and effects of the present disclosure based on the content disclosed in the description. The present disclosure can also be performed or applied by other different execution modes, and the details of the present disclosure each can be imparted with different modifications and alternations based on different views and applications without departing from the scope disclosed by the present disclosure.

All ranges and values recited in the present disclosure are inclusive and combinable. Any value or point falling in the ranges recited herein, such as any integers, can be used as the lower or upper limit to derive a subrange.

It should be noted that the structure, proportion, size, etc., shown in the figures in the specification are only used to match the contents disclosed in the specification for the understanding and reading of those skilled in the art, and are not intended to define the limiting conditions for the implementation of the present disclosure, so they have no technical significance. Any modification of the structure, change of the proportion relationship, or adjustment of the size, without affecting the efficacy and purpose of the present disclosure, should fall in the scope of the technical content disclosed in the present disclosure.

Figure 1:
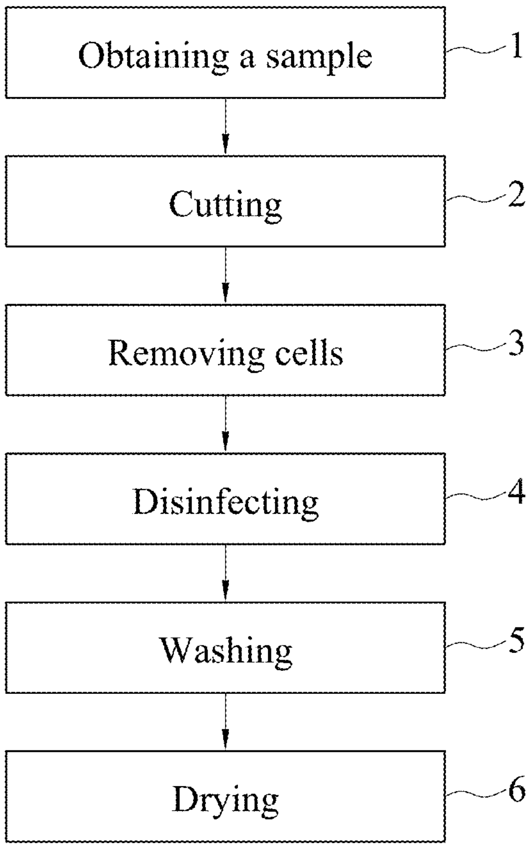
FIG. 1 shows an exemplary flow chart of the method for preparing an intervertebral disc annulus fibrosus implant of the present disclosure.

First, the present disclosure provides an intervertebral disc annulus fibrosus implant and a method for preparing the intervertebral disc annulus fibrosus implant. The method comprises steps of obtaining a sample, cutting, removing cells, disinfecting, drying, etc. The steps were carried out in the order as shown in FIG. 1, i.e., in the order of Step 1: obtaining a sample, Step 2: cutting, Step 3: removing cells, Step 4: disinfecting and Step 6: drying. FIG. 1 also shows an optional Step 5: washing, which, if present, is between Step 4: disinfecting and Step 6: drying.

Regarding Step 1: obtaining a sample, it refers to obtaining a sample having a plurality of ring-shaped collagen fiber layers. In an embodiment, the sample may be derived from an intervertebral disc of a vertebrate, e.g., a spine and an intervertebral disc obtained from a human, a pig, an orangutan, an ape or a monkey; or may be derived from an artificially cultured intervertebral disc annulus fibrosus mimic.

In the present disclosure, Step 2: cutting is cutting unneeded parts from the sample and shaping and trimming the sample into a specific columnar shape. For example, in the case that the sample of Step 1 is derived from a spine of a vertebrate, Step 2 comprises cutting the unnecessary muscle tissue and connective tissue off, taking the intervertebral disc out, and shaping and trimming the intervertebral disc into a column.

The column of the present disclosure refers to a column having a top surface, an opposite bottom surface, and a peripheral surface connecting the top surface and the bottom surface, in which an area of the top surface is smaller than that of the bottom surface and the length (column length) is clearly larger than the maximum width of the bottom surface. The top and the bottom surfaces of the column can be in any shape, e.g., the top and the bottom surfaces are each independently in a circle or a polygon such as a triangle, a quadrilateral, a pentagon, a hexagon, etc. Top and bottom surfaces that are parallel or non-parallel to each other are also included in the scope of the present disclosure. The trimmed sample may have a column length of 8-10 mm, a maximum width of 3-5 mm, for example, a column length of 8, 8.5, 9, 9.5, or 10 mm, and a maximum width of 3, 3.5, 4, 4.5, or 5 mm.

Figure 2:
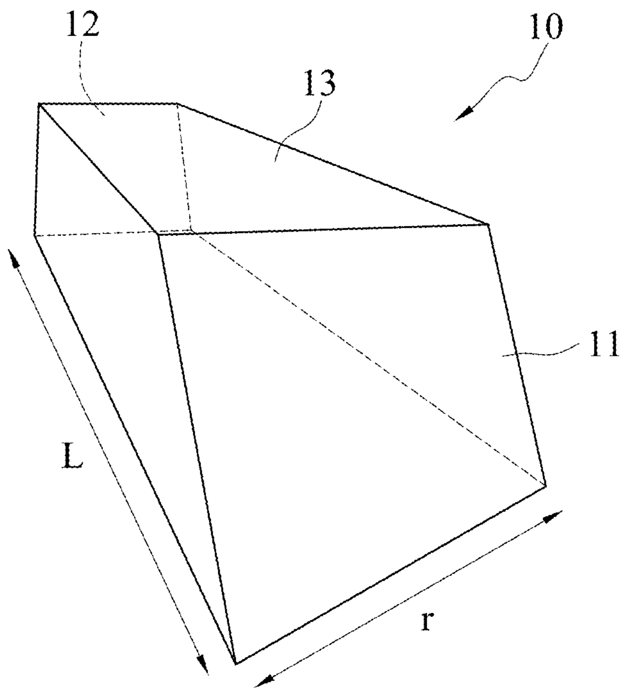
FIG. 2 is an illustrative diagram of the intervertebral disc annulus fibrosus implant of the present disclosure.

FIG. 2 illustrates an example of the column. The sample is cut into a column having a quadrilateral top surface 12, a quadrilateral bottom surface 11, and a peripheral surface 13 connecting the two, wherein the top surface 12 has an area smaller than that of the bottom surface 11, the top and bottom surfaces are not in parallel, and the column length Lis clearly larger than the maximum width r of the bottom surface. The column-shaped sample in FIG. 2 is post-processed as an intervertebral disc annulus fibrosus implant 10. Since damaged wounds in the intervertebral disc annulus fibrosus in the clinic typically appear to be larger inside and smaller outside, the intervertebral disc annulus fibrosus implant should be transplanted with the top surface of the column (with a smaller area) facing outwards and the bottom surface of the column (with a larger area) facing inwards to fit the damage/wound as closely as possible.

Figure 3A:
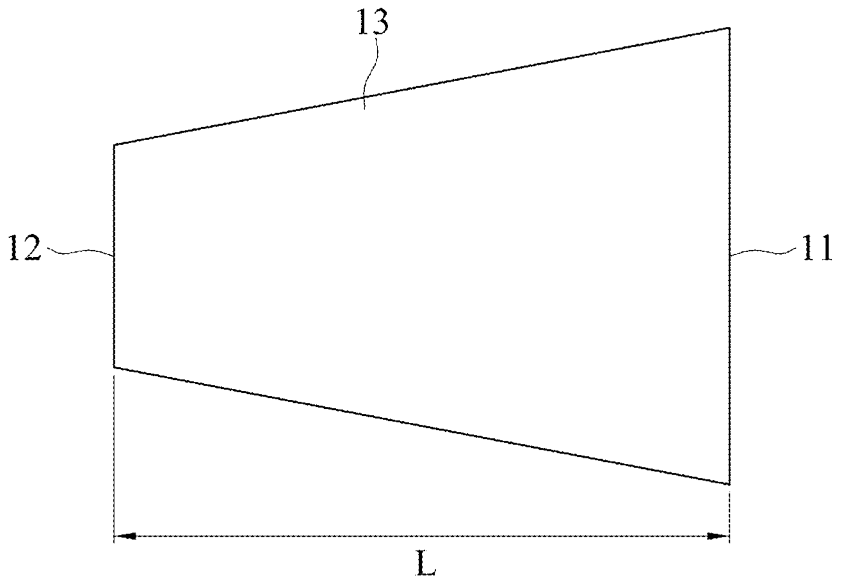
FIG. 3A and FIG. 3B are top-view illustrative diagrams of the peripheral surfaces of two intervertebral disc annulus fibrosus implants of the present disclosure.
Figure 3B:
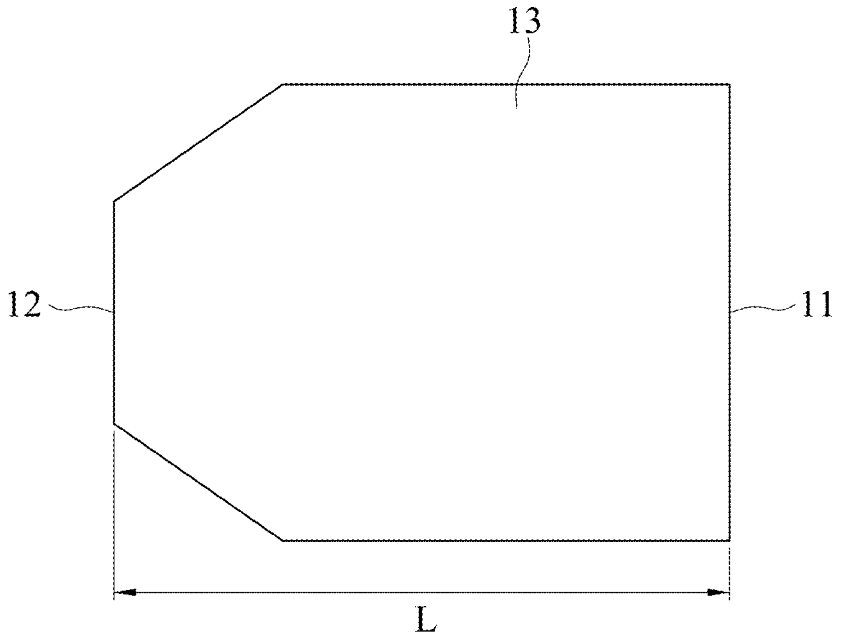
Figure 4:
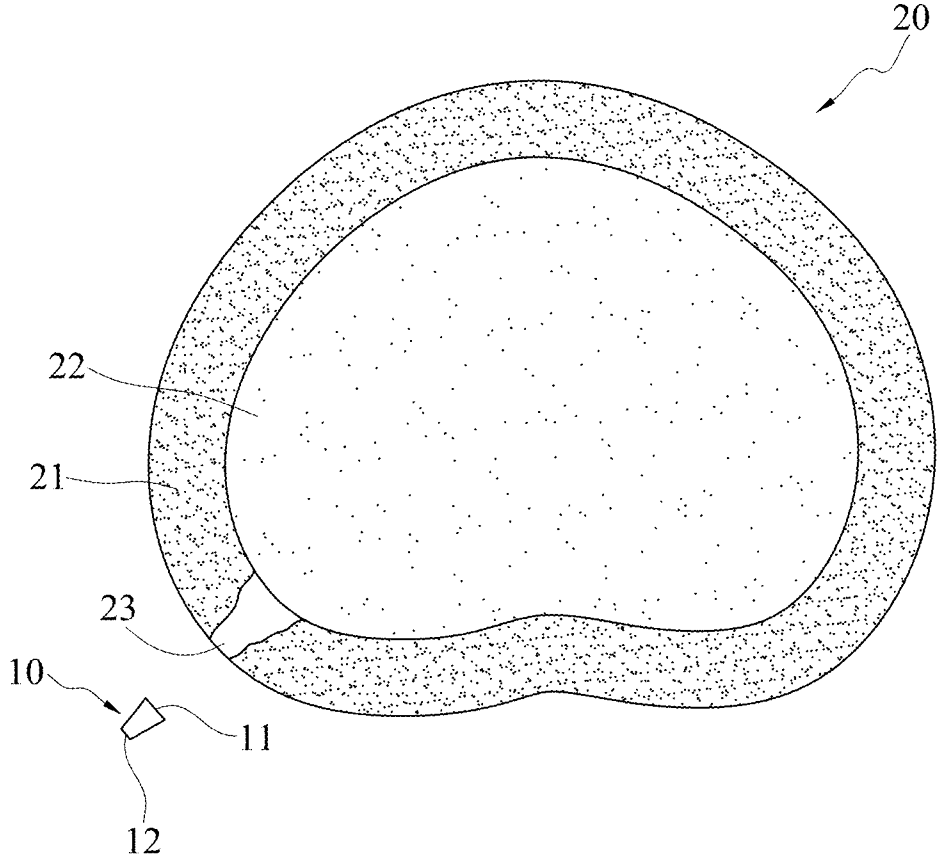
FIG. 4 is an illustrative diagram showing transplanting the intervertebral disc annulus fibrosus implant of the present disclosure to the damaged site in the intervertebral disc annulus fibrosus.

FIG. 3A and FIG. 3B illustrate other examples of the column, and show the top views of the column-shaped intervertebral disc annulus fibrosus implants differing in the peripheral surfaces. In FIG. 3A, the peripheral surface extends straightly from the bottom surface 11 to the top surface 12 and is a continuous straight surface, therefore the top view of the peripheral surface is a trapezoid. In FIG. 3B, the peripheral surface is cut into a non-linearly extending surface from the bottom surface 11 to the top surface 12, therefore the top view of the peripheral surface is in approximated convex irregular hexagon. The shape of the peripheral surface is not limited in the present disclosure, as long as the peripheral surface can connect the top surface and the bottom surface. However, the peripheral surface preferably has reduced sharpness, reduced discontinuity and reduced unevenness, to avoid stimulation and injury to tissues after implantation (as shown in FIG. 4, the stimulation and injury to the wall surface of the damage/wound 23 in the intervertebral disc annulus fibrosus would be caused). Likewise, the top and the bottom surfaces are preferably in a circle, or a polygon of quadrilateral or higher.

In a sample derived from an intervertebral disc of a vertebrate or an artificially cultured intervertebral disc annulus fibrosus mimic, the annulus fibrosus has an uneven composition and structure. An intervertebral disc comprises an intervertebral disc annulus fibrosus and a nucleus pulposus (referring to FIG. 4, an intervertebral disc 20 comprises an intervertebral disc annulus fibrosus 21 and a nucleus pulposus 22). In the ring-shaped collagen fiber layers, the outer portion has higher interlayer density (denser) and the inner portion has lower density (looser); the outer portion has a higher level of Type I collagen and the inner portion has a lower level of Type I collagen; and the outer portion has a lower level of Type II collagen and the inner portion has a higher level of Type II collagen. In an embodiment, the cut sample has a specific orientation according to the uneven composition and structure of the original sample, i.e., the plurality of ring-shaped collagen fiber layers havedervic an interlayer density increased along the direction from the top surface to the bottom surface and/or the Type I collagen content increased along the direction from the top surface to the bottom surface. In order to achieve this orientation, the outer side of the sample is used as the bottom surface and the inner side of the sample is used as the top surface during cutting. After the intervertebral disc annulus fibrosus implant is transplanted at the damage/wound in the intervertebral disc annulus fibrosus, the looser structure of the implant is located at the outer portion to aid wound healing and to promote growth and extension of the newly grown tissues; while the denser structure of the implant is located at the inner portion to achieve a filling effect, so as to prevent the nucleus pulposus from leaking or protruding outwards.

Step 3 of the present disclosure is removing cells from the cut sample, i.e. the column. The column treated with this step is substantially free of cells, indicating that the number of residual cells is reduced to a negligible level or a clinically acceptable level. In an embodiment, removing cells comprises soaking the column in a cell-removal solution containing a surfactant, a chelating agent and saline. Before removing cells, the column may be immersed in saline to maintain moisture. In a further embodiment, the surfactant is at least one selected from the group consisting of 3-cholaminopropyldimethylamino-1-propyl sulfonate (CHAPS), NP-40, Tween-20, Triton X-100 and sodium dodecyl sulfonate (SDS); and the chelating agent is at least one selected from the group consisting of ethylenediaminetetraacetic acid (EDTA), ethylene glycol tetraacetic acid (EGTA) and ethylene diamine. The saline may be phosphate buffer saline (PBS). In still another embodiment, the step is performed for 12 to 24 hours, e.g., 12, 14, 16, 18, 20, 22, or 24 hours. Additionally, the step may be performed on a shaker at a rate of 50-200 rpm, e.g., 50, 100, 150, or 200 rpm.

Step 4 of the present disclosure is disinfecting (or sterilizing), and the column treated with this step is substantially free of microorganisms, indicating that the number of residual microorganisms is reduced to a negligible level or a clinically acceptable level. In an embodiment, disinfecting comprises soaking the column in an antibiotic solution. In a further embodiment, the antibiotic solution comprises amphotericin B, gentamicine and vancomycin. In a further embodiment, the antibiotic solution comprises 2.5 μg/mL of amphotericin B, 50 μg/mL of gentamicine and 500 μg/mL of vancomycin. In still another embodiment, the step is performed for 30 to 60 minutes, e.g., 30, 35, 40, 45, 50, 55, or 60 minutes. Additionally, the step may be performed on a shaker at a rate of 50-200 rpm, e.g., 50, 100, 150, or 200 rpm.

The optional Step 5 of the present disclosure is washing the column to remove the residual treatment solution from the previous step, such as to remove the cell-removal solution and the antibiotic solution. In an embodiment, washing comprises immersing the column in saline solution several times, e.g., 1, 2, 3, or more, each for 30-60 minutes (e.g., 30, 35, 40, 45, 50, 55, or 60 minutes) and each with replacement with new saline solution, and the last washing is for 12-24 hours (e.g., 12, 14, 16, 18, 20, 22, or 24 hours). Additionally, the step may be performed on a shaker at a rate of 50-200 rpm, e.g., 50, 100, 150, or 200 rpm.

Step 6 of the present disclosure is drying the column, and the column treated with this step is substantially free of water, indicating that the amount of residual water is reduced to a negligible level or a clinically acceptable level. In an embodiment, the drying is performed by freeze-drying. In still another embodiment, the drying comprises covering the column with a dust-free cloth to absorb excess liquid, then packaging the column with a packaging material (e.g., Tyvek), freezing for at least 6 hours, and then freeze-drying the column to freeze water and make water sublimate into vapor and escape. In still another embodiment, the step of drying the column also comprises shaping the column to ensure the final shape and size to be desired. In still another embodiment, the column following drying is the final product form of the present disclosure, i.e., an intervertebral disc annulus fibrosus implant, whose size may be a column length of 6-8 mm and a maximum width of 3-5 mm. In still another embodiment, as the intervertebral disc annulus fibrosus implant contacts with water at the target position after implantation, the intervertebral disc annulus fibrosus implant can expand to fill the damaged wound.

Therefore, the method for preparing an intervertebral disc annulus fibrosus implant of the present disclosure comprises:

- obtaining a sample having a plurality of ring-shaped collagen fiber layers;
- cutting the sample into a column, wherein the column has a top surface, an opposite bottom surface, and a peripheral surface connecting the top surface and the bottom surface, wherein an area of the top surface is smaller than that of the bottom surface;
- removing cells from the column;
- disinfecting the column; and
- drying the column to prepare the intervertebral disc annulus fibrosus implant.

The "substantially free of" of the present disclosure comprises the meanings understood by those skilled in the art, such as totally free, nearly free, generally free, etc. In particular, in the case that the content range of a certain component has been specified by a relevant regulation, "substantially free of" is equivalent to or fall into the content range. For example, the intervertebral disc annulus fibrosus implant of the present disclosure is substantially free of microorganisms, which may mean that its sterility assurance level (SAL) is better than 10-6. For another example, the intervertebral disc annulus fibrosus implant of the present disclosure is substantially free of cells, which can refer to being substantially free of cells derived from vertebrates.

The intervertebral disc annulus fibrosus implant of the present disclosure is a column having a plurality of ring-shaped collagen fiber layers. The intervertebral disc annulus fibrosus implant has a top surface, an opposite bottom surface, and a peripheral surface connecting the top surface and the bottom surface, wherein the top surface has an area smaller than that of the bottom surface. The intervertebral disc annulus fibrosus implant is substantially free of cells, water and microorganisms following pretreatments including removing cells, disinfecting and drying.

In order to transplant an intervertebral disc annulus fibrosus implant, the present disclosure also provides a transplanting device and a method for transplanting an intervertebral disc annulus fibrosus implant.

Figure 5:
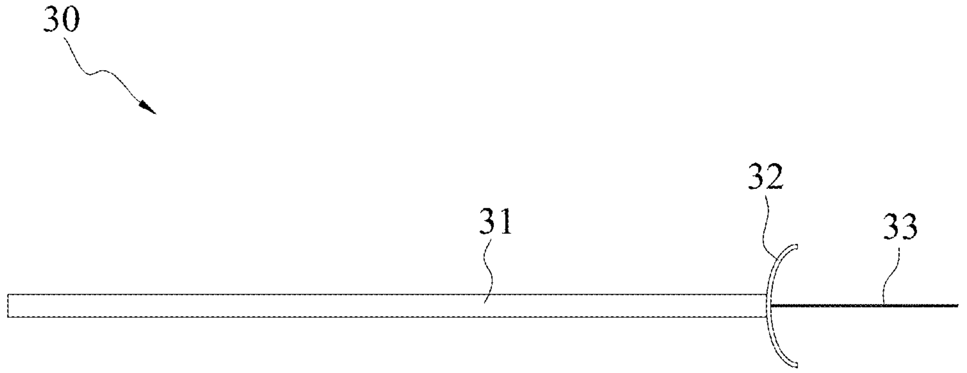
FIG. 5 is an illustrative diagram of the transplanting device of the present disclosure.

As shown in FIG. 5, the transplanting device 30 of the present disclosure comprises a holding part 31, a long needle 33 located on the top of the holding part 31, and a movable base 32 between the holding part 31 and the long needle 33. The long needle 33 is used for inserting to the intervertebral disc annulus fibrosus implant, and the movable base 32 has a through hole (not shown) at the center for the long needle 33 inserting through, thereby allowing the movable base 32 to move along the long needle 33. The intervertebral disc annulus fibrosus implant can be a specific intervertebral disc annulus fibrosus implant described herein or others. In an embodiment, the long needle 33 may be provided with screw thread, preventing it from moving too easily after being inserted into the intervertebral disc annulus fibrosus implant and avoiding the risk of falling off.

Figure 6:
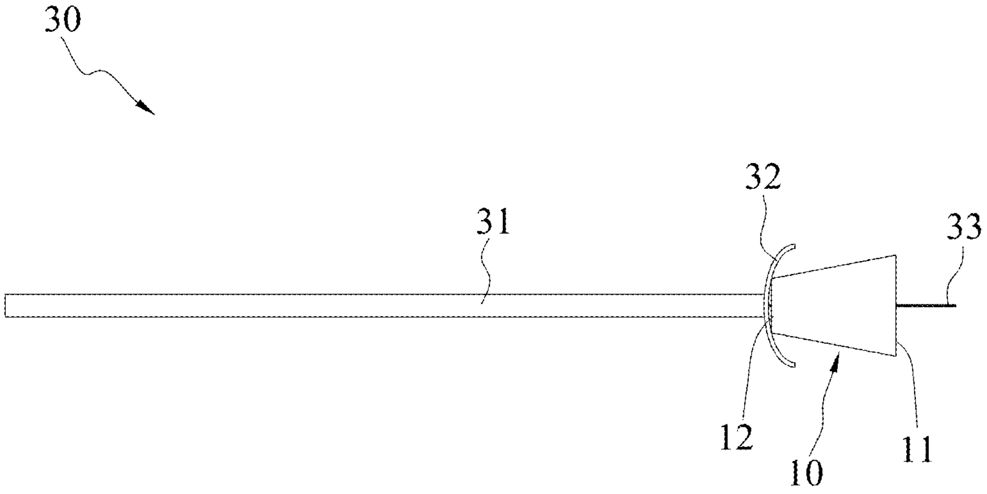
FIG. 6 is an illustrative diagram showing transplanting the intervertebral disc annulus fibrosus implant of the present disclosure by the transplanting device of the present disclosure.

During implantation, as shown in FIG. 6, the long needle 33 is inserted into the through hole of the movable base 32, so that the movable base 32 is located at and against the top of the holding part 31. Then, the long needle 33 is inserted into the intervertebral disc annulus fibrosus implant from the top surface 12 until the top surface 12 of the intervertebral disc annulus fibrosus implant contacts the movable base 32. As shown in FIG. 4, the transplanting device 30 is moved so that the long needle 33 carrying the intervertebral disc annulus fibrosus implant 10 is aimed at the target position, i.e., the damage/wound 23 in the intervertebral disc annulus fibrosus. The transplanting device 30 is continuously moved to make the tip of the long needle 33 enter the damage/wound 23 in the intervertebral disc annulus fibrosus. By moving the movable base 32 along the long needle 33, the intervertebral disc annulus fibrosus implant is pushed in and left at the damage/wound 23 in the intervertebral disc annulus fibrosus (since the volume of the dried intervertebral disc annulus fibrosus implant 10 is smaller than that of the damage/wound 23 in the intervertebral disc annulus fibrosus). In an embodiment, the intervertebral disc annulus fibrosus implant 10, during implantation, contacts with water in the tissue fluid at the target position and expands, and can thus fill the damage/wound 23 in the intervertebral disc annulus fibrosus.

In an embodiment, the movement of the movable base 32 along the long needle 33 may be achieved by holding against the movable base 32 and pulling the long needle 33 out, or by pushing the movable base 32.

Therefore, the method for transplanting an intervertebral disc annulus fibrosus implant of the present disclosure comprises:

- obtaining an intervertebral disc annulus fibrosus implant having a column formed with a plurality of ring-shaped collagen fiber layers, which has a top surface, an opposite bottom surface, and a peripheral surface connecting the top surface and the bottom surface, wherein an area of the top surface is smaller than that of the bottom surface;
- preparing a transplanting device, which comprises a holding part, a long needle located on the top of the holding part, and a movable base between the holding part and the long needle;
- inserting the long needle into the intervertebral disc annulus fibrosus implant from the top surface until the top surface contacts the movable base;
- moving the transplanting device to move the intervertebral disc annulus fibrosus implant to a target position; and
- moving the movable base along the long needle to locate the intervertebral disc annulus fibrosus implant to the target position and leaving it at the target position.

The present disclosure will be illustrated in detail by examples below which are not intended to limit the scope o the present disclosure, i.e., the scope of the present disclosure is not limited by the examples below.

EXAMPLES

A pre-obtained and frozen sample derived from the spine of a Lanyu pig (*Sus scrofa domesticus*) was thawed. The unnecessary muscle and connective tissue were cut off with tools such as a scissor, a scalpel, tweezers, etc. Then, the intervertebral disc annulus fibrosus was found. The side of the scalpel was placed against the edge of the vertebra and slowly cut downward to obtain a sample of the intervertebral disc annulus fibrosus. Next, the sample of intervertebral disc annulus fibrosus was trimmed into a column-shaped sample according to the orientation of the interlayer density of the intervertebral disc annulus fibrosus, wherein the interlayer density of the column increases along a direction from the top surface to the bottom surface, the area of the top surface is smaller than that of the bottom surface, and both of the top and the bottom surfaces are in a quadrilateral shape. The column was washed simply with PBS prior to being immersed in PBS to maintain moisture.

500 mL of cell-removal solution was prepared by mixing SDS, EDTA and PBS. The column was transferred to the cell-removal solution and subjected to a cell-removal step by placing on a shaker and shaking at 120 rpm for 12 hours. Amphotericin B, gentamicin and vancomycin were added to PBS to prepare a 500 mL antibiotic solution containing 2.5 μg/mL of amphotericin B, 50 μg/mL of gentamicin and 500 μg/mL of vancomycin. The column was transferred to the antibiotic solution and subjected to a disinfecting step by placing on a shaker and shaking at 120 rpm for 30 minutes.

The column was taken out and the liquid was thoroughly absorbed with a dust-free cloth. Then, the column was immersed in PBS and placed on a shaker at 120 rpm for 30 minutes. The process was repeated once with the new PBS replaced. Next, the column was taken out and the liquid was thoroughly absorbed with a dust-free cloth, and the column was immersed in PBS and placed on a shaker at 120 rpm for 12 hours. The column was taken out again and the liquid was thoroughly absorbed with a dust-free cloth, and then the column was covered with two layers of Tyvek and frozen for 6 hours for freeze-drying treatment, thereby obtaining a column-shaped intervertebral disc annulus fibrosus implant. The size after drying was 3 mm in diameter and 10 mm in length.

Animal Testing

Experimental animals and sites: Lanyu pig (*Sus scrofa domesticus*); cervical vertebra The pigs were anesthetized, operated and cut at the neck to expose the cervical region. Next, a 3 mm wound was created in the annulus fibrosus of the intervertebral disc to mimic a laceration/damage in the intervertebral disc annulus fibrosus. Two bone anchor screws were wedged into the cervical vertebra at the right-lower and left-lower corners of the wound, and two soft tissue anchor screws were wedged into the intervertebral disc at right-upper and left-upper corners of the wound. Then, the intervertebral disc annulus fibrosus was placed into the wound using a transplanting device with the bottom surface having a large area (with a denser interlayer density of collagen fiber layers and a higher level of Type I collagen) facing inwards and the top surface having a small area (with a looser interlayer density of collagen fiber layers and a lower level Type I collagen) facing outwards. The stitches were tightly fastened by crossing the four anchor screws, ultimately forming a shape where X was located between two parallel "I"'s. X-ray radiography was carried out on the cervical vertebra of the pigs 3 months and 6 months after surgery. The pigs were sacrificed 6 months after surgery and the cervical vertebrae were removed and subjected to HE staining. The result was shown in FIG. 7.

Figure 7:
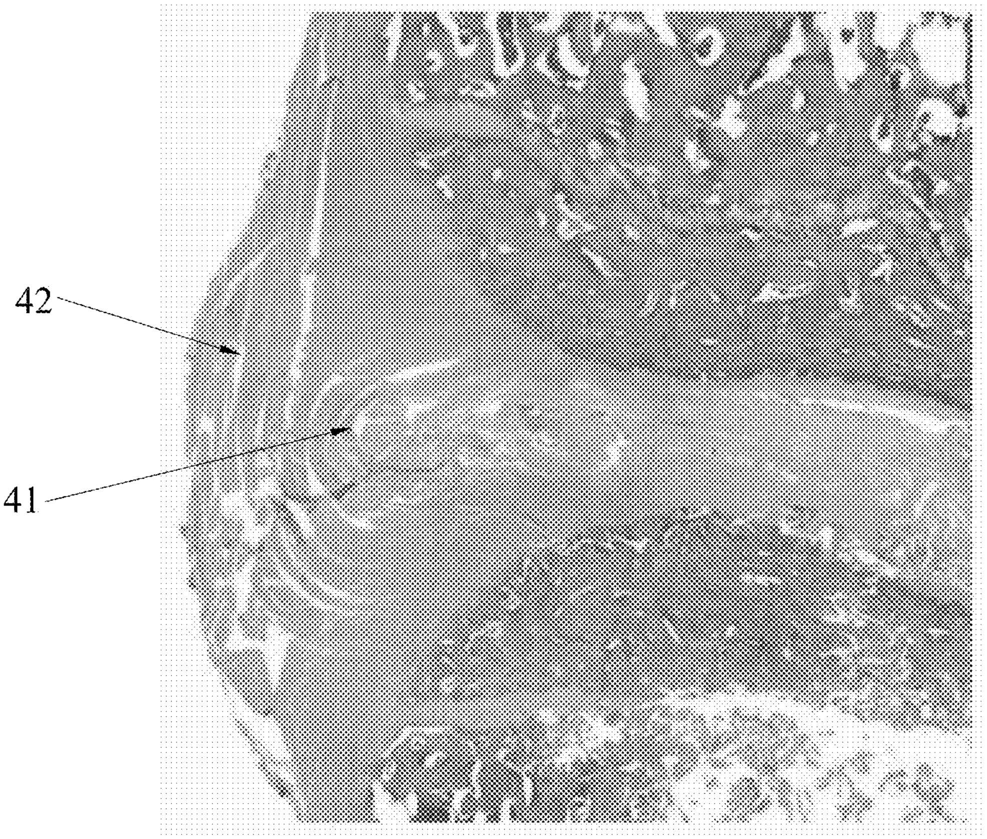
FIG. 7 is a hematoxylin-eosin (HE) staining image of a tissue sample 6 months after the intervertebral disc annulus fibrosus implant of the present disclosure was transplanted into a cervical intervertebral disc of a pig.

According to FIG. 7, it can be seen that newly grown tissue 41 and scar tissue 42 grow after implantation, repairing the wound in the annulus fibrousus (the damage/wound 23 as illustrated in FIG. 4) to effectively prevent the gelatinous substance in the nucleus pulposus from leaking.

According to the disclosure herein, the intervertebral disc annulus fibrosus implant of the present disclosure can be used for impairing the damage in intervertebral disc annulus fibrosus, and has effects of unease displacement after transplantation and preventing the gelatinous substance in the nucleus pulposus from leaking or protruding. The method for transplanting an intervertebral disc annulus fibrosus implant of the present disclosure can transplant the implant rapidly and exactly, and can effectively fix the implant by placing it at the transplanting site in a particular manner.

What is claimed is:

1. An intervertebral disc annulus fibrosus implant, the implant comprising a column having a plurality of ring-shaped collagen fiber layers, wherein the column has a top surface, an opposite bottom surface, and a peripheral surface connecting the top surface and the bottom surface, wherein an area of the top surface is smaller than that of the bottom surface, and the intervertebral disc annulus fibrosus implant is substantially free of cells, water and microorganisms, wherein the plurality of ring-shaped collagen fiber layers have an interlayer density increased along a direction from the top surface to the bottom surface.

2. The intervertebral disc annulus fibrosus implant of claim 1, wherein the top surface and the bottom surface are each independently circular or polygonal.

3. The intervertebral disc annulus fibrosus implant of claim 1, wherein the plurality of ring-shaped collagen fiber layers have a type I collagen content increased along a direction from the top surface to the bottom surface.

4. The intervertebral disc annulus fibrosus implant of claim 1, wherein the intervertebral disc annulus fibrosus implant is derived from an intervertebral disc of a vertebrate or an artificially cultured intervertebral disc annulus fibrosus mimic.

5. The intervertebral disc annulus fibrosus implant of claim 1, wherein the column has a length of 6-10 mm and a maximum width of 3-5 mm.

6. A method for transplanting an intervertebral disc annulus fibrosus implant, comprising:

obtaining an intervertebral disc annulus fibrosus implant of claim 1;

preparing a transplanting device, which comprises a holding part, a long needle located on the top of the holding part, and a movable base between the holding part and the long needle;

inserting the long needle into the intervertebral disc annulus fibrosus implant from the top surface until the top surface contacts the movable base;

moving the transplanting device to move the intervertebral disc annulus fibrosus implant to a target position; and moving the movable base along the long needle to locate the intervertebral disc annulus fibrosus implant to the target position and leaving it at the target position.

* * * * *